United States Patent
Fujisaki et al.

(10) Patent No.: US 11,109,881 B2
(45) Date of Patent: Sep. 7, 2021

(54) ULTRASOUND DEVICE AND ULTRASOUND DEVICE SYSTEM USED FOR ANCHOR FIXATION AND ANCHOR FIXATION METHOD USING ULTRASOUND DEVICE

(71) Applicant: OLYMPUS CORPORATION, Hachioji (JP)

(72) Inventors: Ken Fujisaki, Sagamihara (JP); Takamitsu Sakamoto, Hachioji (JP); Takeo Usui, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 314 days.

(21) Appl. No.: 16/394,118

(22) Filed: Apr. 25, 2019

(65) Prior Publication Data
US 2019/0247079 A1    Aug. 15, 2019

Related U.S. Application Data

(63) Continuation of application No. PCT/JP2016/082186, filed on Oct. 28, 2016.

(51) Int. Cl.
*A61B 17/32* (2006.01)
*A61B 17/16* (2006.01)
*A61C 3/03* (2006.01)
*A61B 17/56* (2006.01)
*A61C 8/00* (2006.01)

(52) U.S. Cl.
CPC ...... *A61B 17/320068* (2013.01); *A61B 17/16* (2013.01); *A61B 17/1615* (2013.01); *A61B 17/1624* (2013.01); *A61B 17/32* (2013.01); *A61B 17/56* (2013.01); *A61C 3/03* (2013.01);
(Continued)

(58) Field of Classification Search
CPC ............................................. A61B 17/320068
See application file for complete search history.

(56) References Cited

U.S. PATENT DOCUMENTS

2004/0267269 A1    12/2004  Middleton et al.
2006/0195107 A1     8/2006  Jones et al.
(Continued)

FOREIGN PATENT DOCUMENTS

JP    H10-295700 A    11/1998
JP    2001-079013 A    3/2001
(Continued)

OTHER PUBLICATIONS

Jan. 10, 2017 International Search Report issued in International Patent Application No. PCT/JP2016/082186.

*Primary Examiner* — Andrew Yang
(74) *Attorney, Agent, or Firm* — Oliff PLC

(57) ABSTRACT

Ultrasound oscillation can be propagated to a distal end of an elongated probe. A cross-sectional surface of the probe is perpendicular to the length of the probe, and has to the same shape as a shape of a cross-sectional surface of an anchor. The probe is configured to form a bottomed hole in a bone for placing the anchor and the shape of its cross-sectional surface can prevent rotation of the anchor in the bottomed hole. An area of the cross-sectional surface of the probe at the distal end can be larger than an area of a cross-sectional surface of the probe at a proximal end. The distal end of the probe includes a treatment portion that extends outward from a center of the proximal end of the probe in a first direction perpendicular to the longitudinal direction and in a second direction different from the first direction.

12 Claims, 19 Drawing Sheets

(52) U.S. Cl.
CPC . *A61B 2017/320072* (2013.01); *A61C 8/0089* (2013.01)

(56) References Cited

U.S. PATENT DOCUMENTS

| | | |
|---|---|---|
| 2006/0253050 A1 | 11/2006 | Yoshimine et al. |
| 2009/0125071 A1 | 5/2009 | Skinlo et al. |
| 2010/0063541 A1 | 3/2010 | Brunelle et al. |
| 2010/0167235 A1 | 7/2010 | Vercellotti et al. |
| 2016/0113779 A1 | 4/2016 | Neubardt |

FOREIGN PATENT DOCUMENTS

| | | |
|---|---|---|
| JP | 2008-528242 A | 7/2008 |
| JP | 2010-504138 A | 2/2010 |
| JP | 2015-534898 A | 12/2015 |
| WO | 2006/030563 A1 | 3/2006 |
| WO | 2014/077920 A1 | 5/2014 |

ULTRASOUND DEVICE AND ULTRASOUND DEVICE SYSTEM USED FOR ANCHOR FIXATION AND ANCHOR FIXATION METHOD USING ULTRASOUND DEVICE

CROSS-REFERENCE TO RELATED APPLICATION

This application is a continuation of International Application No. PCT/JP2016/082186, filed on Oct. 28, 2016, the entire contents of which are incorporated herein by reference.

BACKGROUND

The present disclosure relates to an ultrasound device and an ultrasound device system used for anchor fixation and an anchor fixation method using the ultrasound device.

Typically, anchor fixation is performed as an orthopedic procedure for restoring damaged labrum glenoidale (shoulder, hip joint) or torn ligament (shoulder, ankle, knee, elbow, wrist, or the like). Anchor fixation uses a suture anchor. The suture anchor includes a suture and a fixing tool (anchor); the anchor is fixed to a bone, and ligaments or tendons are bundled and secured with the suture. Suture anchors can be a screw type and a hammering type, and they can be made of a material such as titanium or polyether ether ketone (PEEK) resin. Usually, a bottomed hole for placing a suture anchor is previously formed in a bone by using a drill to prevent the occurrence of cracks or breakage in the bone while the suture anchor is screwed or hammered.

Furthermore, ultrasound treatment devices that form a hole for fixing an artificial bone in a bone using ultrasound oscillations with a bone processing tool can require two projections provided at the distal end of the probe.

SUMMARY

According to exemplary embodiments, a medical ultrasound device used for fixation using an anchor is provided. The medical ultrasound device can include an ultrasound generator configured to generate ultrasound oscillation; and an elongated probe having a proximal end and a distal end. Ultrasound oscillation can be propagated from the ultrasound generator to the proximal end, and continue to be propagated toward the distal end in a longitudinal direction of the probe. A cross-sectional surface of the probe at the distal end has the same shape as a shape of a cross-sectional surface of the anchor. The probe is configured to form a bottomed hole in a bone for placing the anchor and has a shape that can prevent rotation of the anchor in the bottomed hole. An area of the cross-sectional surface of the probe at the distal end is larger than an area of a cross-sectional surface of the probe at the proximal end.

The above and other features, advantages and technical and industrial significance of this disclosure will be better understood by reading the following detailed description of exemplary embodiments of the disclosure, when considered in connection with the accompanying drawings.

DETAILED DESCRIPTION

With reference to drawings, an explanation is given below of a surgery system including an ultrasound device according to an embodiment of the disclosure and suture-anchor fixation for the surgery system. The present embodiment is fixation for fixing a suture anchor for restoring a torn ligament (each joint) or damaged labrum glenoidale (shoulder, hip joint) by using the ultrasound device.

Figure 1:
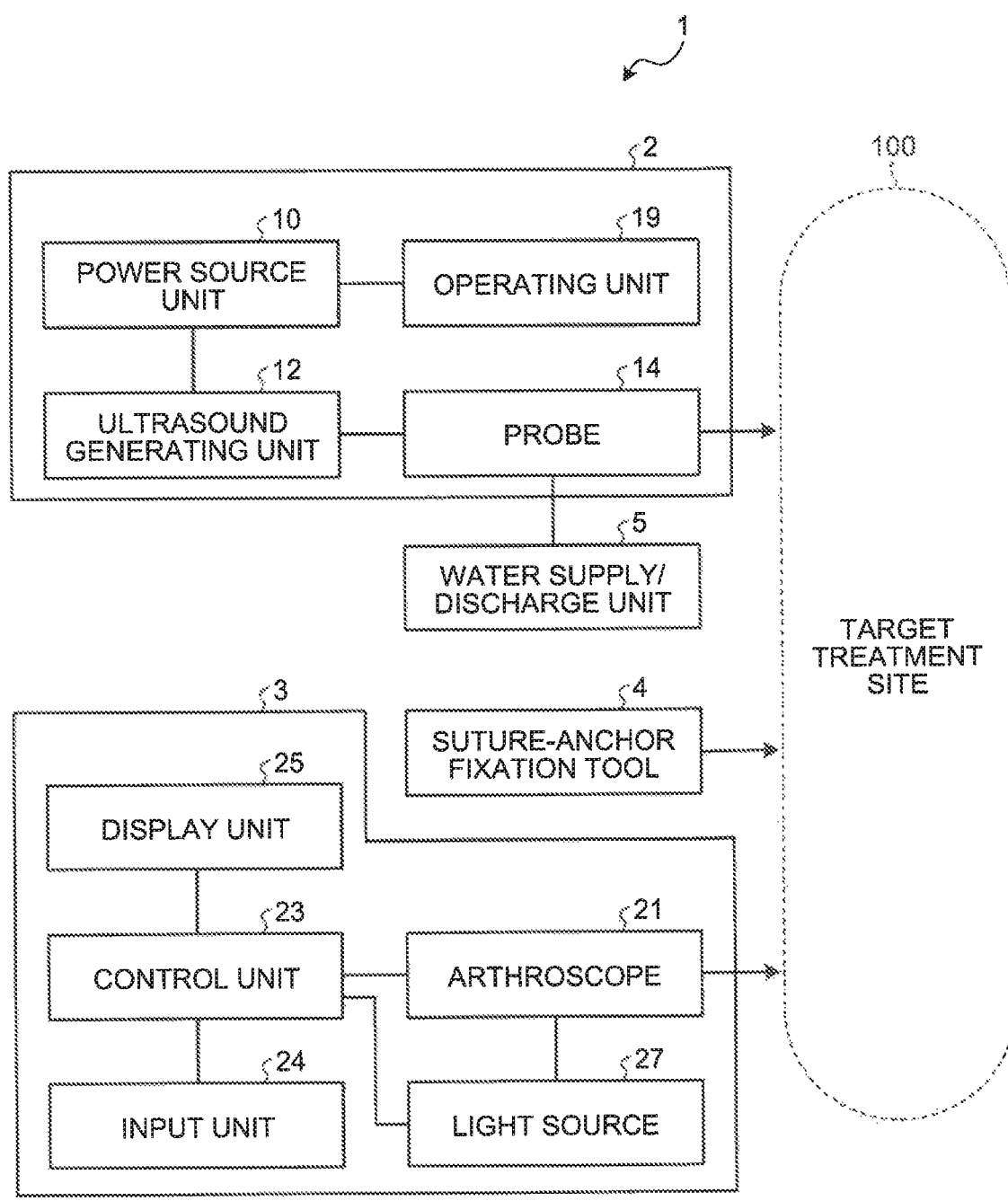
FIG. 1 illustrates an example of the configuration of a surgery system including an ultrasound device according to an exemplary embodiment.
Figure 2:
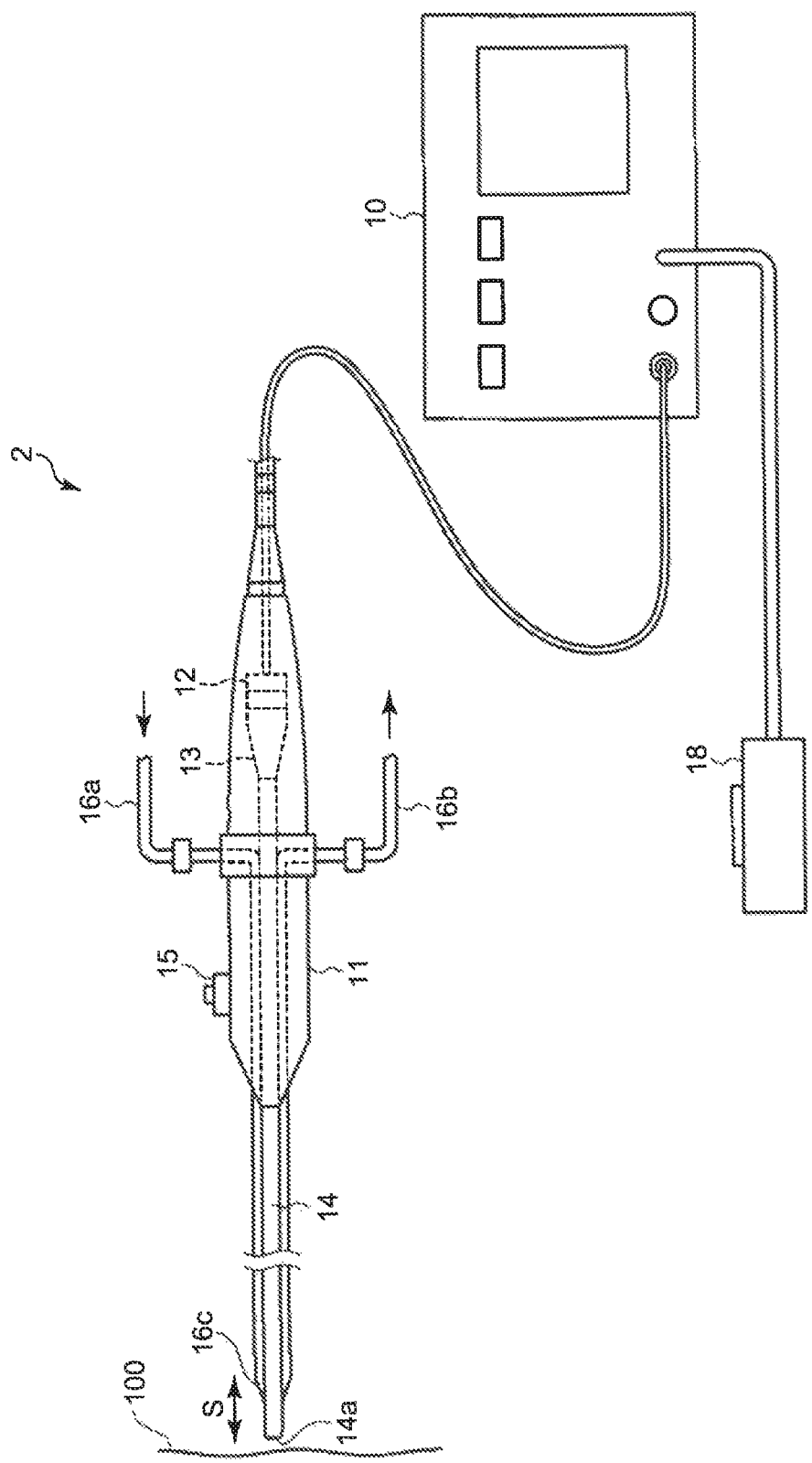
FIG. 2 is a diagram that illustrates an example of the configuration of the ultrasound device in the surgery system.

FIG. 1 illustrates an example of the configuration of the surgery system including the ultrasound device according to the present embodiment. FIG. 2 is a diagram that illustrates an example of the configuration of the ultrasound device in the surgery system.

A surgery system 1 according to the present embodiment includes: an ultrasound device 2; an endoscope system 3 including an arthroscope 21; a suture-anchor fixation tool 4 that fixes a suture anchor; and a water supply/discharge unit 5 that supplies and discharges a perfusion fluid including saline, or the like. When the suture-anchor fixation is implemented during an operative incision, the endoscope system 3 and the water supply/discharge unit 5 are not essential.

The ultrasound device 2 includes: an ultrasound generating unit (oscillating unit) 12 that generates ultrasound oscillations by using an ultrasound transducer (e.g., piezoelectric element); an elongated probe 14 that conducts a resection treatment to form a bottomed hole in the target treatment site by transmitting ultrasound oscillations; a power source unit 10 that supplies a drive power to the ultrasound generating unit 12; and an operating unit 19 that turns on/off generation of ultrasound oscillations. The ultrasound device 2 uses ultrasound oscillations to conduct incision treatment or resection treatment on the target treatment site, for example soft tissue or bone (subchondral bone, or the like).

The water supply/discharge unit 5 supplies and discharges a perfusion fluid to the periphery including the target treatment site through the ultrasound device 2. According to the present embodiment, a configuration is such that water is supplied and discharged through the water supply/discharge unit 5; however, a configuration may be such that water is supplied and discharged through the endoscope system 3. In the following explanation, the direction along the longitudinal axis of the elongated probe 14 is referred to as a longitudinal direction.

The endoscope system 3 is used when the suture-anchor fixation is executed through a portal, and it includes: the arthroscope 21 that is a rigid endoscope, which is one type of endoscope; as a light source for illumination light, a visible light source 27 that emits visible illumination light; a control unit 23 that performs overall control of the endoscope system 3; an input unit 24 such as keyboard or touch panel; and a display unit 25 that displays surgery information including captured surgery situations.

Figure 7A:
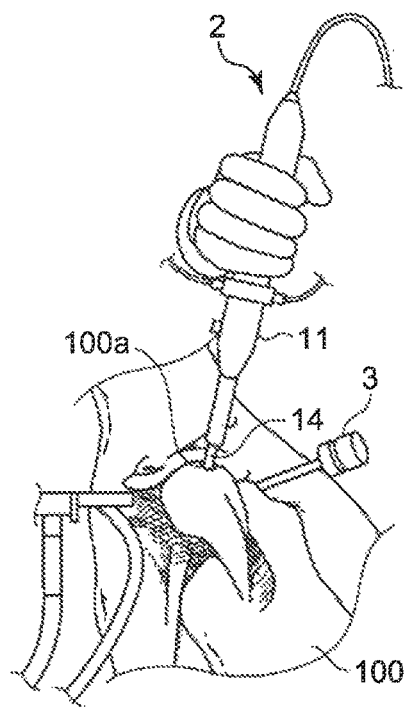
FIG. 7A is a diagram that illustrates a state where the bottomed hole for placing the suture anchor is formed by using the ultrasound device.
Figure 7B:
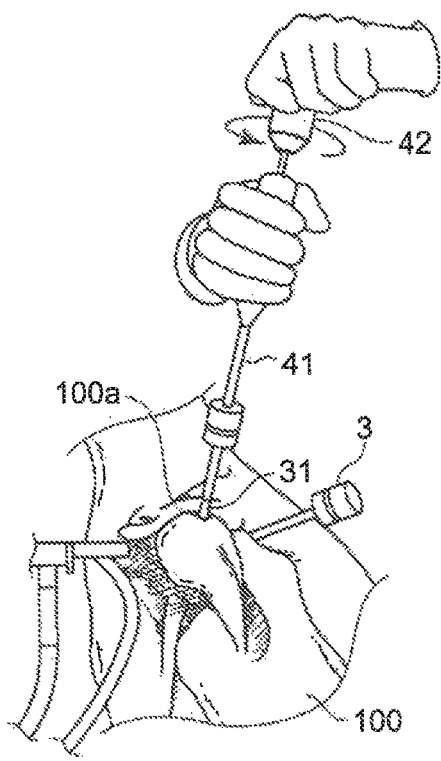
FIG. 7B is a diagram that illustrates a state where the suture anchors are fixed to the bottomed hole with the suture-anchor fixation tool.

As illustrated in FIG. 7B described later, the suture-anchor fixation tool 4 includes an anchor fixing tool 41 that places and fixes the anchor of the suture anchor in a bottomed hole formed in a bone; and suture fixing devices (passers, or the like) 43, 44 that fix sutures to the anchor so as to bundle or sew a ligament or labrum glenoidale.

The ultrasound device 2 according to the present embodiment is explained in detail.

As illustrated in FIG. 2, the ultrasound device 2 according to the present embodiment includes: a device main body 11 including the ultrasound generating unit 12 and the probe 14; the power source unit 10; and a foot switch 18 that gives a command to turn on/off ultrasound oscillations. The device main body 11 and the power source unit 10 are coupled to each other via a cable so as to supply drive power and communicate control signals.

The device main body 11 includes: the ultrasound generating unit 12 that is formed in a cylindrical shape to be grasped by an operator and that includes an ultrasound transducer (piezoelectric body, or the like) inside it; the elongated probe 14 whose proximal end side is sonically connected to the ultrasound generating unit 12 through a horn 13; a distal end 14a that is provided at the distal end of the probe and functions as a treatment portion that conducts cutting; an operating switch 15 that is provided on the device main body 11 and gives a command to turn on/off ultrasound oscillations; and flow paths 16a, 16b for supplying and discharging a perfusion fluid from the water supply/discharge unit 5. The foot switch 18 has a function equivalent to that of the operating switch 15.

Figure 3:
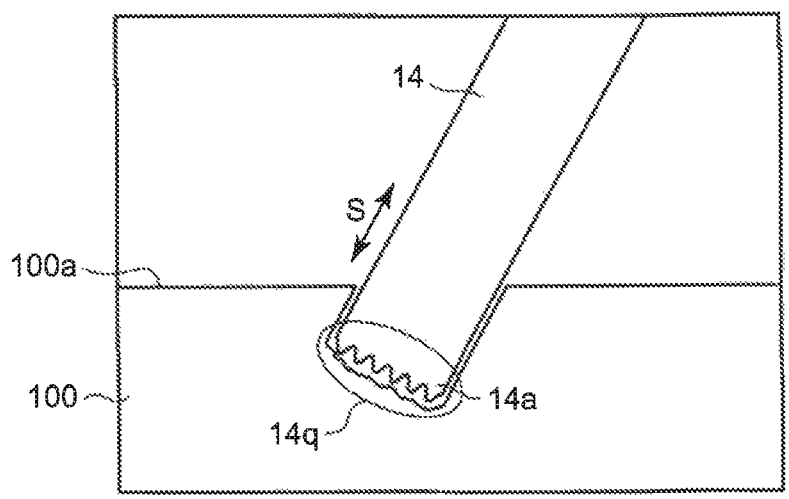
FIG. 3 is a diagram that illustrates the state of cutting with a probe that vibrates with ultrasound waves.
Figure 4:
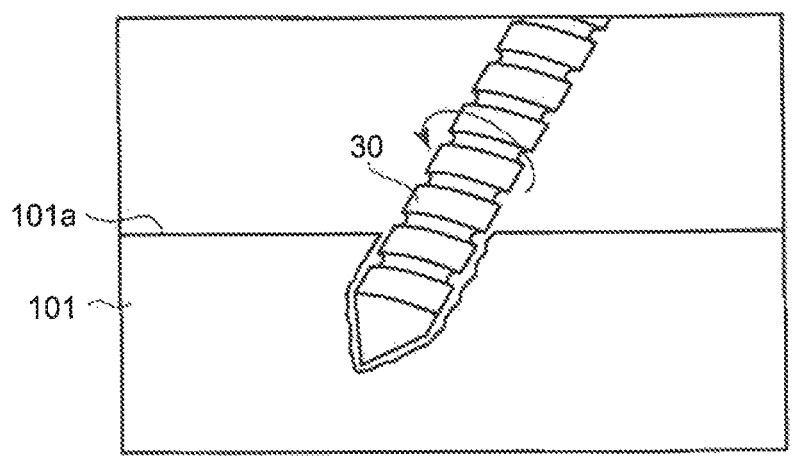
FIG. 4 is a diagram that illustrates the state of cutting with the rotary blade of a rotary drill.

With reference to FIG. 3 and FIG. 4, an explanation is given of the probe 14 of the ultrasound device according to the present embodiment and a difference in the treatment state depending on the rotary blade of a drill. FIG. 3 is a diagram that illustrates the state of cutting with the probe that vibrates with ultrasound waves, and FIG. 4 is a diagram that illustrates the state of cutting with the rotary blade of a rotary drill.

As illustrated in FIG. 3, the probe 14 oscillates with ultrasound waves and is provided with a plurality of peaks and troughs 14q on the distal end surface of the distal end 14a. The probe 14 performs an oscillating action to move back and forth in the longitudinal direction of the probe so that it has a mechanical cutting function (hammering) for crushing by beating with the abutting distal end 14a in an oscillation direction s.

Figure 6A:
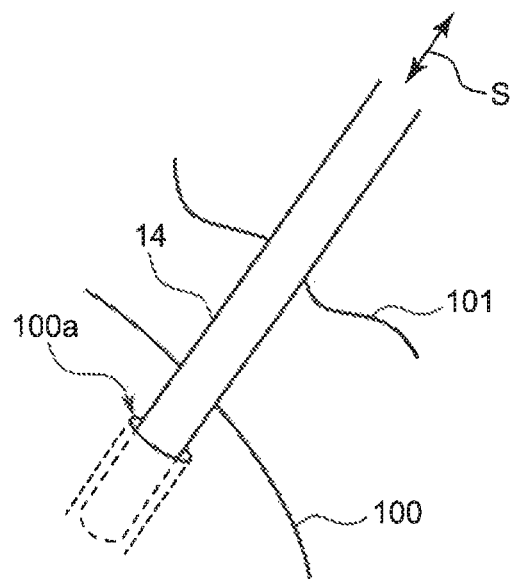
FIG. 6A is a diagram that illustrates a state where a probe of the ultrasound device forms a bottomed hole in the target treatment site (bone)

Furthermore, due to cutting during a hammering operation, only the area abutting the distal end 14a of the probe 14 is beaten with micro oscillations and is mechanically scraped; thus, it is possible to form a hole having the shape identical to that of the probe 14 in cross-section. For example, as illustrated in FIG. 6A, the use of the probe 14 having a circular shape in cross-section forms, in a target treatment site 100, a bottomed hole 100a having the same circular shape as that of the probe 14. However, as illustrated in FIG. 4, cutting with a rotary blade 30 of the drill causes cracks around the hole or streaky bumps and fuzz on the cut surface (the wall surface of the hole) that has been scraped.

Figure 5A:
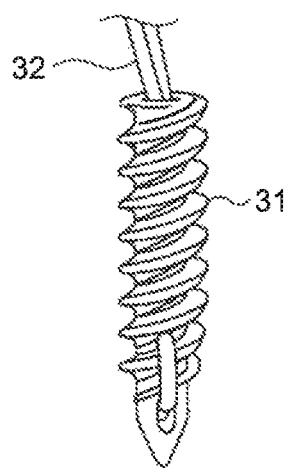
FIG. 5A is a diagram that illustrates an external configuration of a screw-type suture anchor.
Figure 5B:
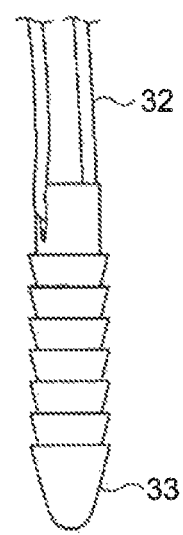
FIG. 5B is a diagram that illustrates an external configuration of a hammering-type suture anchor.

Next, with reference to FIG. 5A, 5B to FIG. 9, the suture-anchor fixation using the ultrasound device according to the present embodiment is explained. Here, FIG. 5A is a diagram that illustrates an external configuration of a screw-type suture anchor, and FIG. 5B is a diagram that illustrates an external configuration of a hammering-type suture anchor.

A helical screw thread is formed on the circumference of a screw-type suture anchor 31. Ring-shaped conical projections are formed on the circumference of a hammering-type suture anchor 33 such that they are continuous in the longitudinal direction. The conical projections are formed at the distal end side in the direction toward which they are tapered. Furthermore, at least two sutures 32 are secured to the rear end of each of the suture anchors 31, 33. As the materials of the suture anchors 31, 33, titanium, polyether ether ketone (PEEK) resin, or the like, is used. However, there is no particular limitation as long as it is a rigid material usable for medical purposes.

Figure 6B:
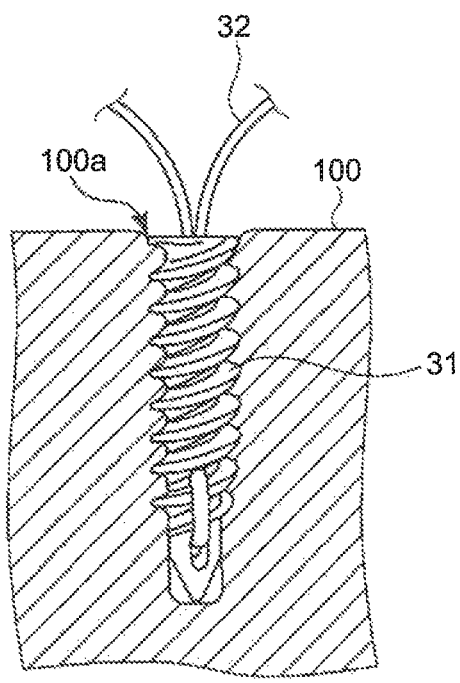
FIG. 6B is a diagram that illustrates a state where a suture anchor is placed and fixed in the formed bottomed hole.

FIG. 6A is a diagram that illustrates a state where the probe 14 of the ultrasound device 2 forms the bottomed hole 100a in the target treatment site (bone) 100. FIG. 6B is a diagram that illustrates a state where the suture anchor 31 (33) is placed and fixed in the formed bottomed hole 100a.

Figure 7C:
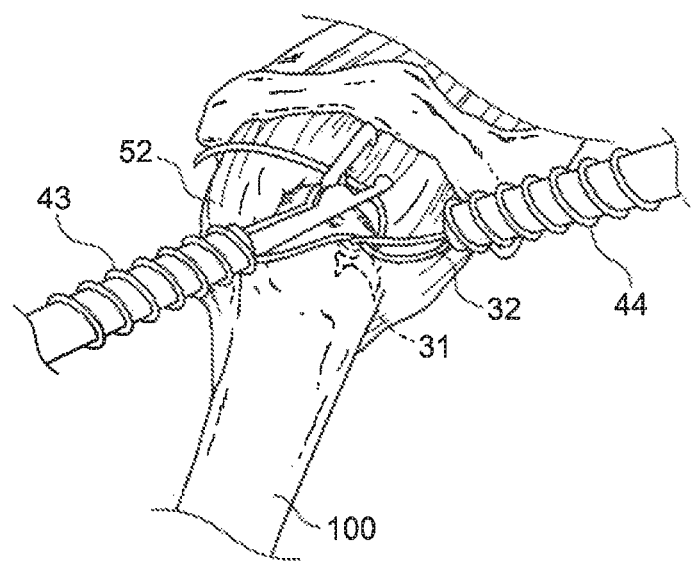
FIG. 7C is a diagram that illustrates a state where torn ligaments are bundled with sutures by using a dedicated tool.
Figure 7D:
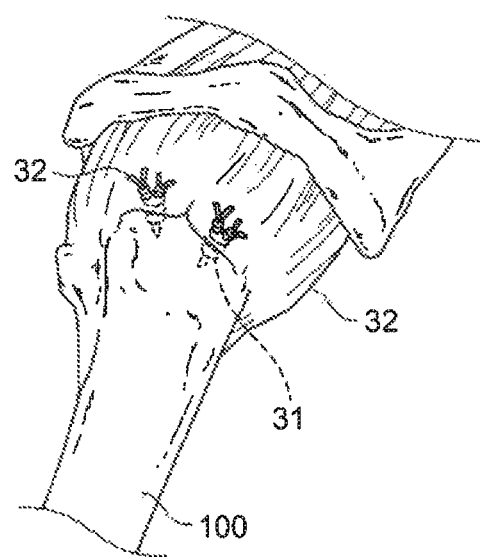
FIG. 7D is a diagram that illustrates a state of the ligament fixed with the suture anchors after fixation.
Figure 8:
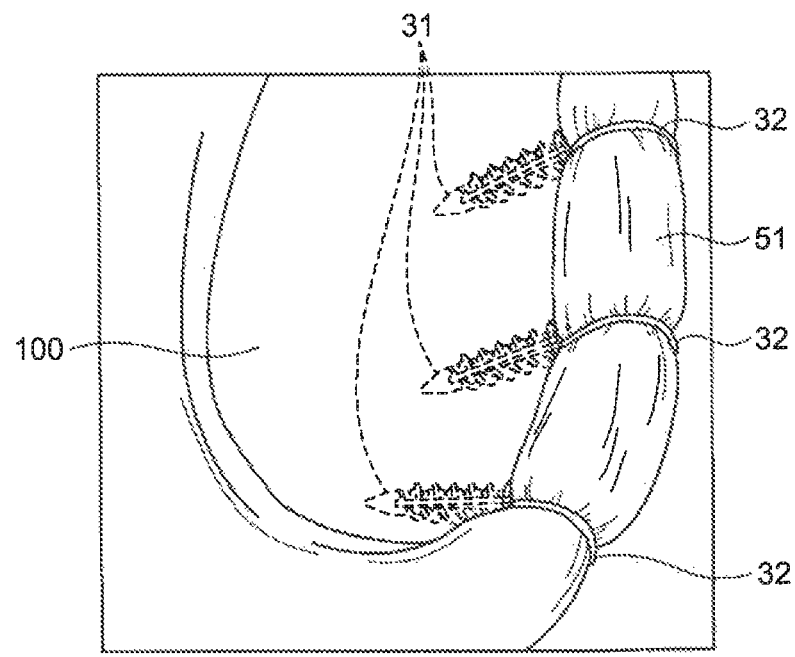
FIG. 8 is a diagram that illustrates an example where a damaged labrum glenoidale is fixed to the bone part of a glenoid cavity with suture anchors.
Figure 9:
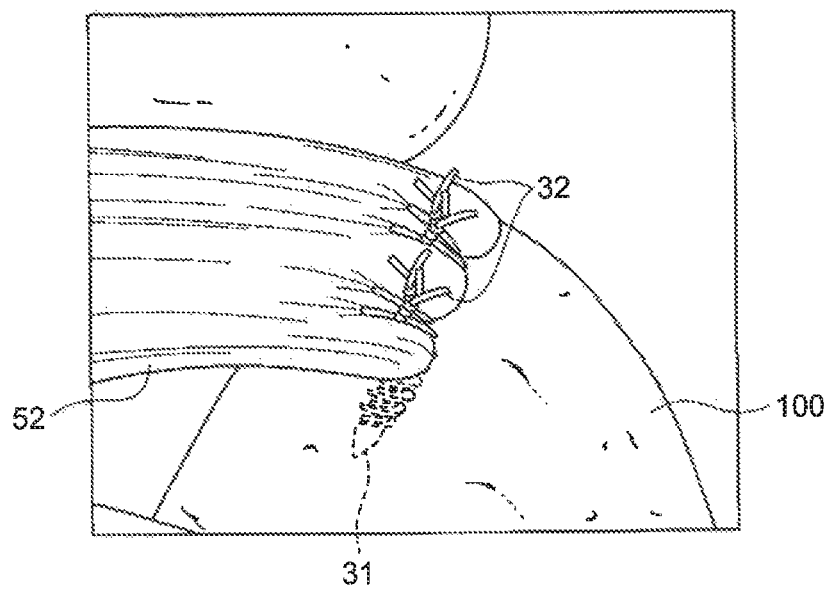
FIG. 9 is a diagram that illustrates an example where a torn ligament is fixed to a bone with suture anchors.

FIG. 7A is a diagram that illustrates a state where the bottomed hole 100a for placing the suture anchor 31 (33) is formed by using the ultrasound device 2, and FIG. 7B is a diagram that illustrates a state where the suture anchors 31, 33 are fixed to the bottomed hole with the suture-anchor fixation tool 4. FIG. 7C is a diagram that illustrates a state where torn ligaments are bundled with sutures by using a dedicated tool. FIG. 7D is a diagram that illustrates a state of the ligament fixed with the suture anchors after fixation. FIG. 8 is a diagram that illustrates an example where a damaged labrum glenoidale (shoulder or hip joint) is fixed to the bone part of a glenoid cavity with suture anchors. FIG. 9 is a diagram that illustrates an example where a torn ligament is fixed to a bone with suture anchors.

FIG. 7A illustrates for example an arthroscopic surgery; an undepicted portal, which is a small hole, is formed on two or three areas, and the ultrasound device 2 and the endoscope system 3, which is an arthroscope, are inserted. Then, while the periphery of the target treatment site is filled with a perfusion fluid including saline, or the like, a video displayed on the monitor is checked, and the suture-anchor fixation is executed. In this example, a perfusion fluid flows into the periphery of a treatment area.

First, at the first producing step, as illustrated in FIG. 6A and FIG. 7A, to form the bottomed hole 100a in a bone 100 covered with soft tissue 101 by using the probe 14 of the ultrasound device 2, the probe 14 is pressed against the soft tissue 101 in the longitudinal direction s toward the formation position of a bottomed hole. Here, as the probe 14 is not rotated, it moves forward by resecting the soft tissue 101 without involving the peripheral soft tissue, and it reaches the bone 100. Continuously, the probe 14 is pressed against the bone 100 to perform a hammering operation, and it gradually moves in by crushing the bone 100 in the area of the abutting point of the distal end of the probe, thereby forming the bottomed hole 100a.

Then, at the second producing step, as illustrated in FIG. 7B, the suture anchor 31 is attached to a predetermined position on the distal end of the anchor fixing tool 41. The distal end of the anchor fixing tool 41 is inserted into the formed bottomed hole 100a, and a handle 42 is operated so that the suture anchor 31 is screwed and fixedly placed in the bottomed hole 100a. Then, the anchor fixing tool 41 is removed while the suture anchor 31 is left in the bottomed hole 100a.

Then, at the third producing step, as illustrated in FIG. 7C, a torn ligament 52 is sewed with a suture 32 for treatment by using the suture fixing devices (passers, or the like) 43, 44, and it is ligated as illustrated in FIG. 7D, whereby fixing treatment with the suture anchor 31 is finished.

FIG. 8 illustrates an example where a damaged labrum glenoidale (shoulder or hip joint) 51 is fixed to the bone part of a glenoid cavity with the suture anchor 31 by using the suture-anchor fixation according to the present embodiment. In this example, it is necessary to fix a labrum glenoidale to the edge portion of the bone 100 of the recessed glenoid cavity. When a bottomed hole is formed with a drill, there is a possibility that impact from the rotary blade causes damages such as cracks or breakage.

According to the present embodiment, gradual cutting with ultrasound oscillations reduces effects (damages, or the like) on the periphery of a bottomed hole; a hole may be formed near the edge of a glenoid cavity, and the setting of the direction in which a bottomed hole is formed may be relatively flexible. The shape and the direction of a bottomed hole may be the shape and the direction corresponding to the stress applied to the suture anchors 31, 33.

FIG. 9 illustrates an example where, by using the suture-anchor fixation according to the present embodiment, the torn ligament 52 is secured to the bone with the suture anchors 31, 33 such that it is sewed. The use of the suture anchors for securing and running from the sutures 32 to the ligament enables a high securing force and fastening such that the force for securing the ligament is distributed.

The ultrasound device can form a bottomed hole for the suture anchor, whereby it is possible to prevent unintentional damages to a bone during screwing or hammering of the suture anchor.

Furthermore, in the bottomed hole formed by using ultrasound oscillations, the anchor is not rotated due to torque received from the suture; the suture anchor is not loosened relative to the bottomed hole, and the bone is properly regenerated, whereby formation of the bone is promptly started after treatment. Moreover, the probe of the ultrasound device conducts cutting due to ultrasound oscillations without being rotated; therefore, to form a bottomed hole in a bone, even formation of a bottomed hole starts at soft tissue that is present on the bone, the soft tissue is prevented from being involved due to the rotary blade of the drill as is conventionally done, a drill guide is not necessary, and a treatment at a narrow space is possible.

Furthermore, in order to form a hole in the rigid treatment target such as bone, a drill blade needs to ensure a certain degree of strength, which causes a difficulty in reducing the diameter of the drill blade and accordingly in reducing the diameter of the bottomed hole. Furthermore, it is possible to easily form a bottomed hole with a small angle relative to the bone surface, and it is possible to fix the suture anchor at a desired angle relative to each treatment target.

The shape of the bottomed hole for fixing the suture anchor is not limited to the circular shape of the bottomed hole 100a in cross-section. According to the present embodiment, examples of the configuration of a probe for forming a bottomed hole having a different shape are explained below.

Figure 10A:
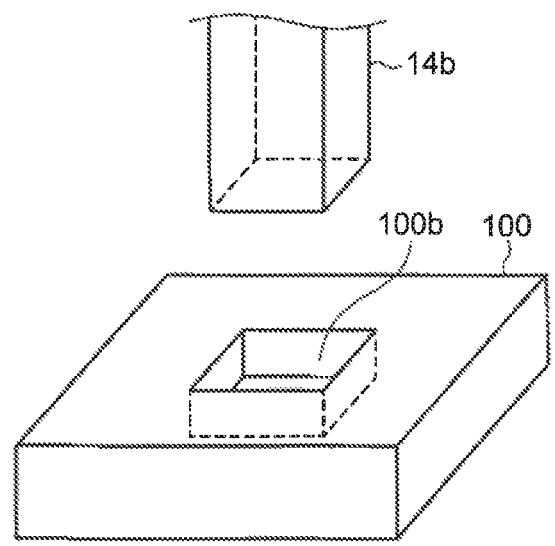
FIG. 10A is a diagram that illustrates a rectangular probe according to an exemplary embodiment.

In FIG. 10A, a probe 14b can have a rectangular distal end in cross-section forms, in the target treatment site 100, a rectangular bottomed hole 100b that is the same as the distal end of the probe 14b.

Figure 10B:
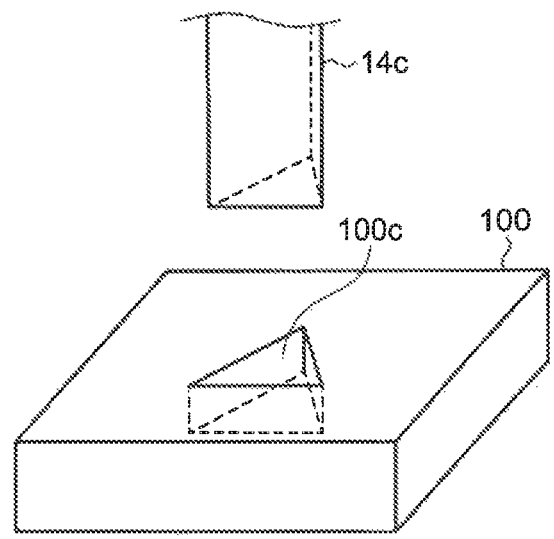
FIG. 10B is a diagram that illustrates a triangular probe according to an exemplary embodiment.

In FIG. 10B, a probe 14c can have a triangular distal end in cross-section forms, in the bone 100, a triangular hole 100c that is the same as the distal end of the probe 14c.

Figure 10C:
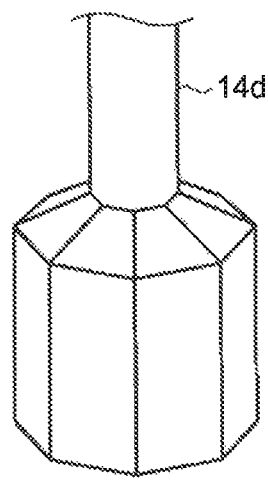
FIG. 10C is a diagram that illustrates a polygonal probe according to an exemplary embodiment.

FIG. 10C illustrates a probe 14d that is polygonal more than a triangle, here octagonal, in cross-section.

Figure 10D:
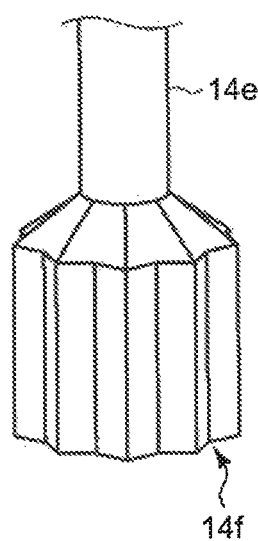
FIG. 10D is a diagram that illustrates a polygonal probe according to an exemplary embodiment.

Furthermore, FIG. 10D illustrates a probe 14e in which a recess 14f is formed on each surface of the polygon illustrated in FIG. 10C. The polygon described in the present embodiment includes the shape having the recessed surface (depressed surface) illustrated in FIG. 10D, and for example, a shape like a star is also referred to as a polygon.

Figure 10E:
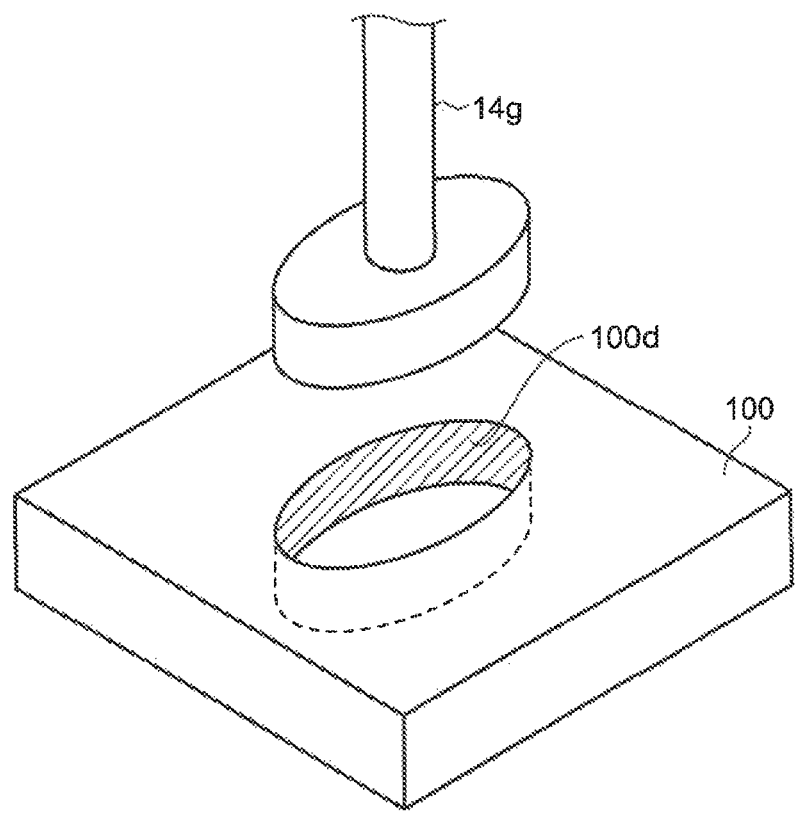
FIG. 10E is a diagram that illustrates an elliptical probe according to an exemplary embodiment.

In FIG. 10E, a probe 14g having an elliptical distal end in cross-section forms, in the target treatment site 100, an elliptical bottomed hole 100d that is the same as the distal end of the probe 14g. It is formed in a conic curve including not only an elliptical shape but also a semi-circular shape, and the like.

Figure 10F:
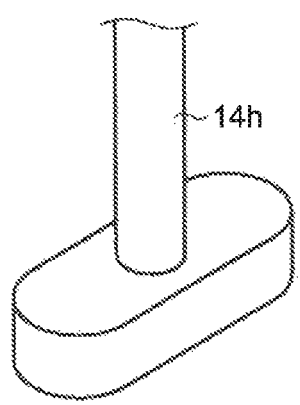
FIG. 10F is a diagram that illustrates a probe shaped like a track according to an exemplary embodiment.

FIG. 10F illustrates a probe 14h having an oval shape, e.g., a rectangle with rounded corners (track shape), in cross-section.

Figure 10G:
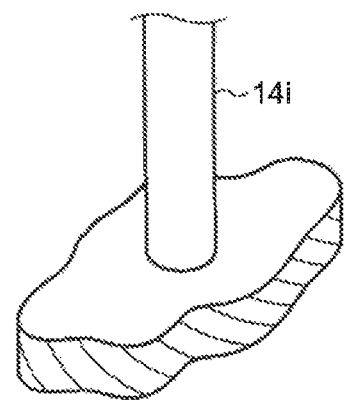
FIG. 10G is a diagram that illustrates a probe having an irregular shape according to an exemplary embodiment.

FIG. 10G illustrates a probe 14i having an irregular shape, that is, the circumference of the cross-sectional surface is the continuous combination of partial circles having different curvatures. Here, it is an irregular shape combining partial circles; furthermore, it may be an irregular shape combining corner parts having different angles, or it may be an irregular shape combining a circular part and a corner part.

Figure 10H:
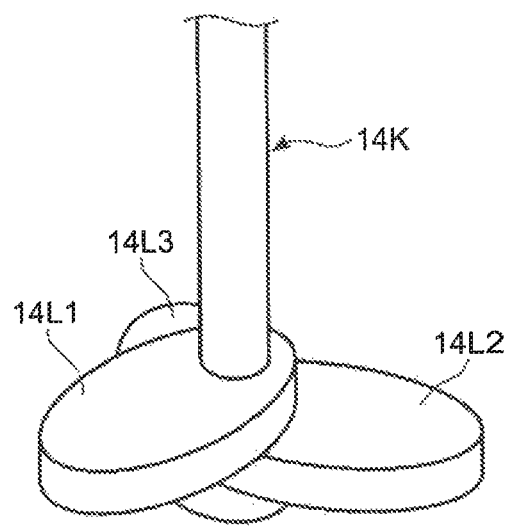
FIG. 10H is a diagram that illustrates an elliptical probe having a stack of multiple layers according to an exemplary embodiment.

Furthermore, FIG. 10H illustrates the external configuration of a probe 14K. A configuration is such that three probes 14L1, 14L2, 14L3, which are elliptical in cross-section, are overlapped on one another, a shaft is inserted through the probes at one end side along the longitudinal axis of the ellipse, and the probes are spread, at different levels, such that they are equiangularly partitioned relative to the circle. In this example, the probes 14L1, 14L2, 14L3 are arranged equiangularly at an angle of 120°.

Figure 10I:
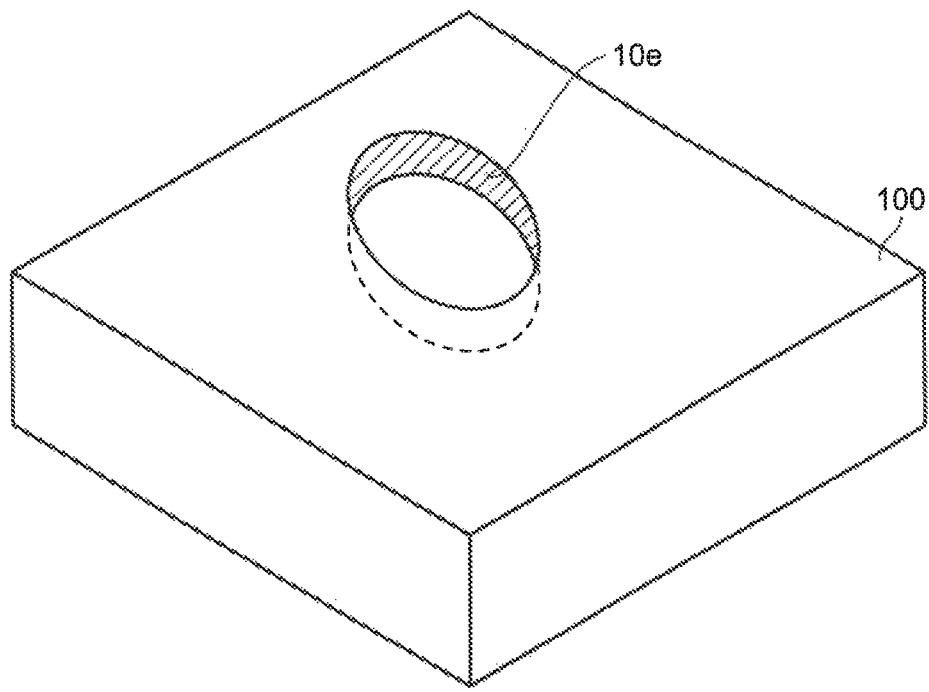
FIG. 10I is a diagram that illustrates an external configuration of an elliptical bottomed hole formed with a probe that is on the first layer.
Figure 10J:
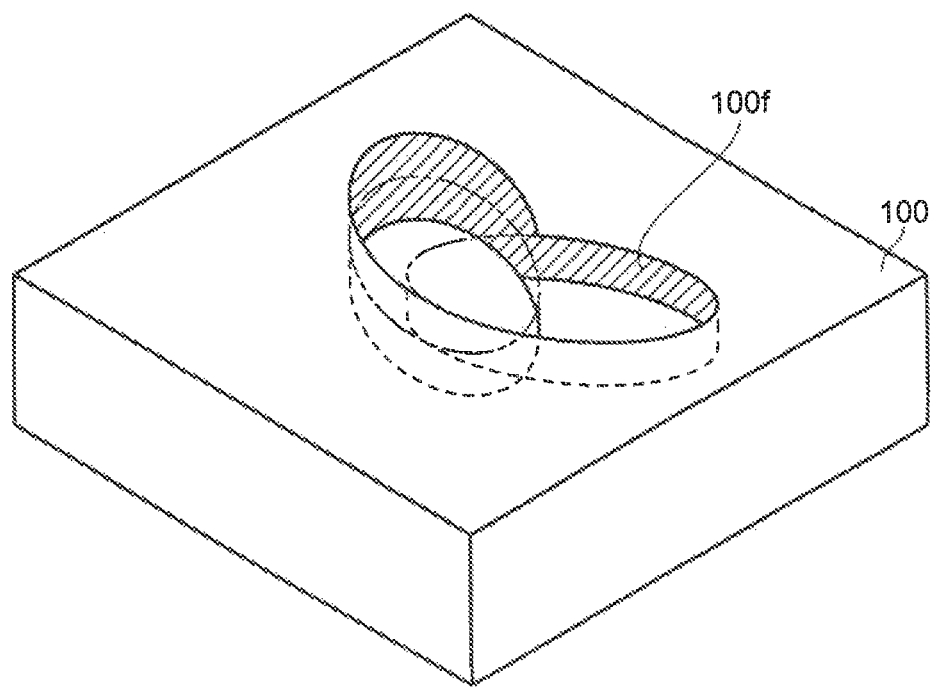
FIG. 10J is a diagram that illustrates an external configuration of elliptical bottomed holes formed with probes that are on the first layer and the second layer.
Figure 10K:
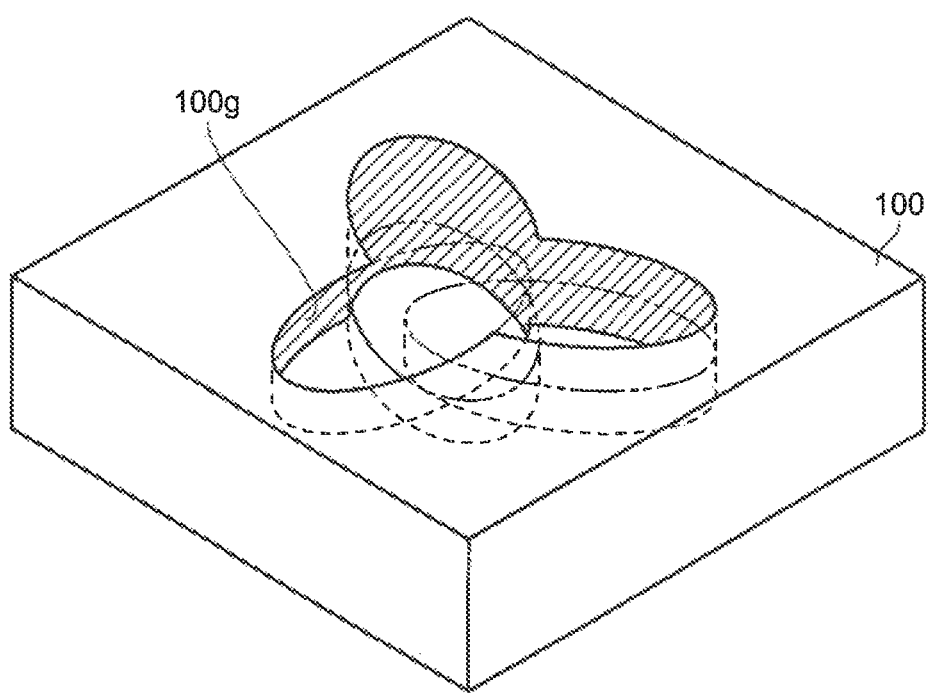
FIG. 10K is a diagram that illustrates an external configuration of elliptical bottomed holes formed with probes that are on the first to the third layers.

With reference to FIG. 10I to FIG. 10K, bottomed holes formed with the probe 14K is explained. FIG. 10I is a diagram that illustrates an elliptical bottomed hole formed with the probe 14L3 that is on the first layer of the probe 14K, FIG. 10J is a diagram that illustrates bottomed holes formed with the probes 14L3, 14L2 that are on the first and the second layers of the probe according to the eighth configuration example, and FIG. 10K is a diagram that illustrates bottomed holes formed with the probes 14L3, 14L2, 14L1 that are on the first to the third layers of the probe according to the eighth configuration example.

After the probe 14L3 of the probe 14K, which oscillates with ultrasound waves, is first pressed against the bone 100 for resection, an elliptical bottomed hole 10e is formed as illustrated in FIG. 10I. The probe 14K is continuously pressed, and the elliptical probe 14L2 on the second layer is brought into contact with the bone 100 so that it starts resection. After resection with the probe 14K is continued, an elliptical bottomed hole 100f whose angle has been rotated by 120° is formed on the bottomed hole 10e having a deeper depth, as illustrated in FIG. 10J. The probe 14K is further pressed, and the probe 14L1 is brought into contact with the bone 100 so that it starts resection, and as illustrated in FIG. 10K, a bottomed hole 100g is formed with an equal angular interval in addition to the bottomed holes 10e, 100f.

As described above, the circular shape of the probe according to the present embodiment includes a shape formed in a conic curve including an elliptical shape, a semi-circular shape, and the like, a shape combining a straight line and a curved line, e.g., an elongated circular (track) shape, and further as a different shape of a circle, a rectangular shape with rounded corners. Furthermore, it may be a shape including at least one angle, such as a shape smaller than a fan-like shape or a semi-circular shape, e.g., a ¼ circular shape. Furthermore, these shapes include shapes combining not only protruding surfaces but also recessed surfaces such as cutout.

By using the probe 14 that has a polygonal shape more than a triangle, a bottomed hole having a polygonal shape more than a triangle in cross-section is formed. A suture anchor placed in these bottomed holes is preferably the hammering-type suture anchor 33.

Figure 10L:
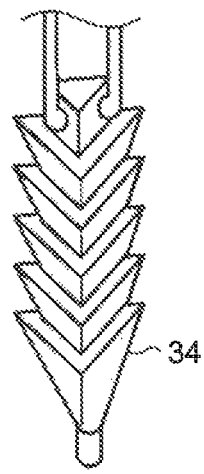
FIG. 10L is a diagram that illustrates an external configuration of a hammering-type suture anchor having a triangular shape in cross-section.
Figure 10M:
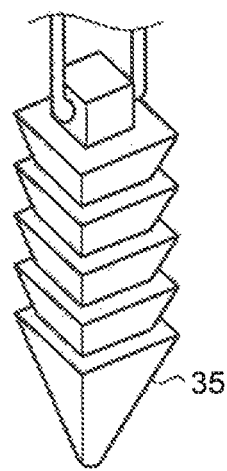
FIG. 10M is a diagram that illustrates an external configuration of a hammering-type suture anchor having a rectangular shape in cross-section.

As illustrated in FIG. 5B, in the anchor part of the suture anchor 33, the ring-shaped conical projections are formed on the circumference thereof such that they are continuous in the longitudinal direction. For this reason, the circular bottomed hole causes a problem of rotation due to received torque. However, when the polygonal probes 14b, 14c, which are rectangular or triangle as illustrated in FIG. 10A and FIG. 10B, are used, suture anchors 34, 35 having the same shapes as the polygonal shapes illustrated in FIG. 10L and FIG. 10M are placed so that they are prevented from being rotated even when receiving torques as the corner parts are engaged.

According to the present embodiment, rotation of the suture anchors 34, 35 after placement is preventable as a bottomed hole for placing a suture anchor is formed in cross-section in a circular shape other than an exact circle and a different shape including a polygonal shape, or the like, and a suture anchor is formed in the shape corresponding to the shape of the bottomed hole.

Furthermore, the load (tension) applied to the fixed suture anchor from the bundled ligament, or the like, has directional characteristics. In the case of a suture anchor that is circular in cross-section, it has an equal strength in the direction in which tension is not applied. Specifically, there is no problem if the maximum strength is obtained in the direction in which tension is applied and the normal strength is maintained in a direction in which tension is not applied, e.g., a direction perpendicular to the direction in which tension is applied.

In an example where a suture anchor having a triangular shape in cross-section is hammered and fixed into a bottomed hole, one of the surfaces of the triangle is disposed in a direction perpendicular to the direction in which tension is applied, and the surface of the suture anchor is disposed in the direction in which tension is applied, whereby the strength against tension may be improved. The shape of a bottomed hole may be a shape having the strength corresponding to the stress applied to the suture anchor.

Figure 11A:
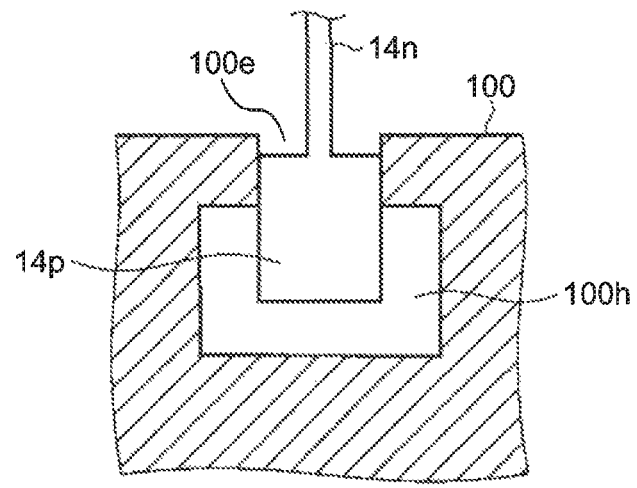
FIG. 11A is a diagram that conceptually illustrates a bottomed hole for placing a suture anchor and a probe according to an exemplary embodiment.
Figure 11B:
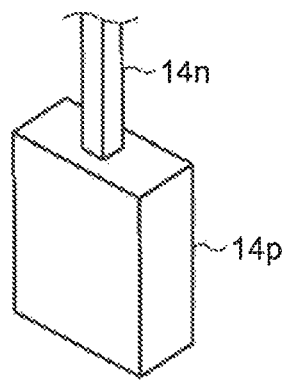
FIG. 11B is a diagram that illustrates an external configuration of a probe.
Figure 12A:
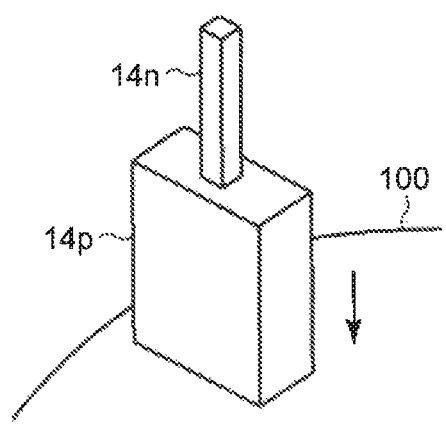
FIG. 12A is a diagram that illustrates a state where the probe is pressed against the bone.
Figure 12B:
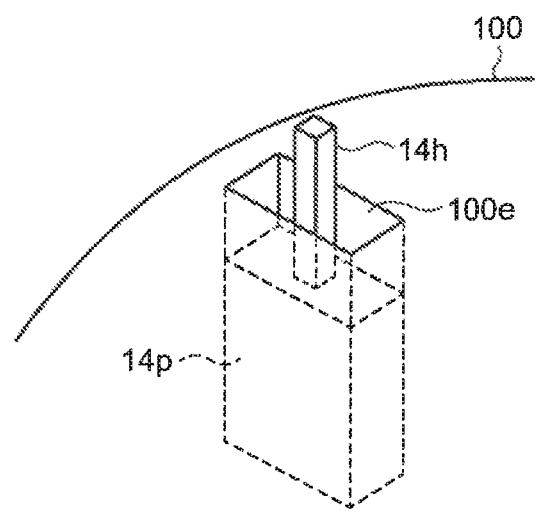
FIG. 12B is a diagram that illustrates a longitudinal hole formed inside the bone with the probe.
Figure 12C:
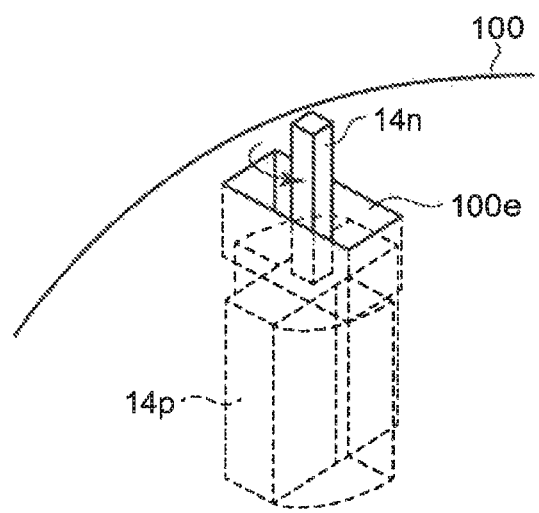
FIG. 12C is a diagram that illustrates a state where the probe is rotated inside the longitudinal hole.
Figure 12D:
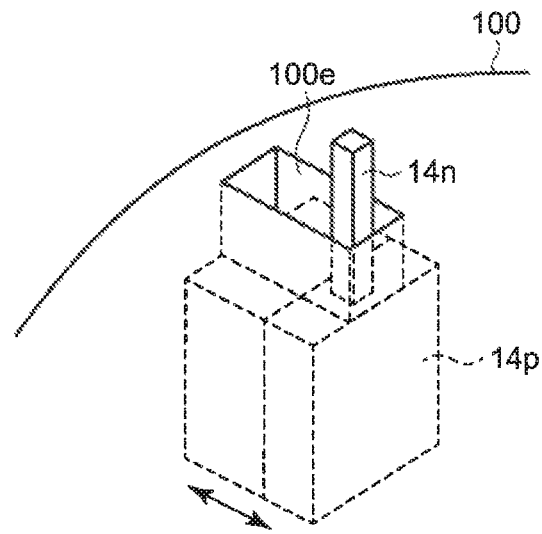
FIG. 12D is a diagram that illustrates a state where the bottomed hole is formed with the probe.
Figure 13A:
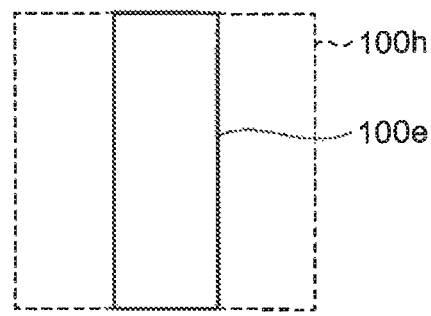
FIG. 13A is a conceptual diagram when the formed bottomed hole is viewed in the direction of an hole entrance.
Figure 13B:
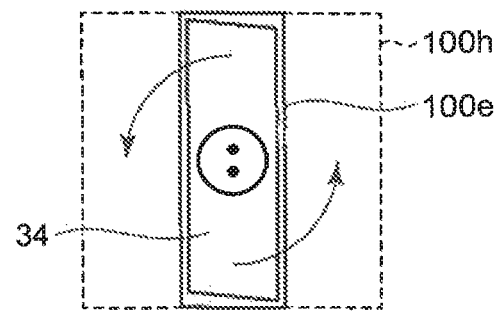
FIG. 13B is a diagram that illustrates a state where the suture anchor is inserted into the bottomed hole.
Figure 13C:
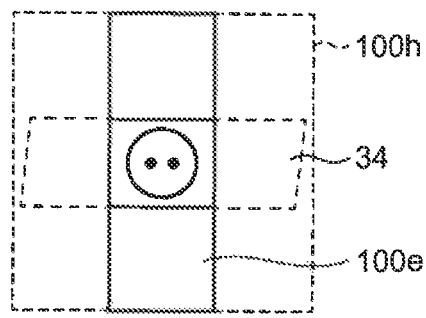
FIG. 13C is a diagram that illustrates a state where the suture anchor inserted into the bottomed hole is rotated.
Figure 13D:
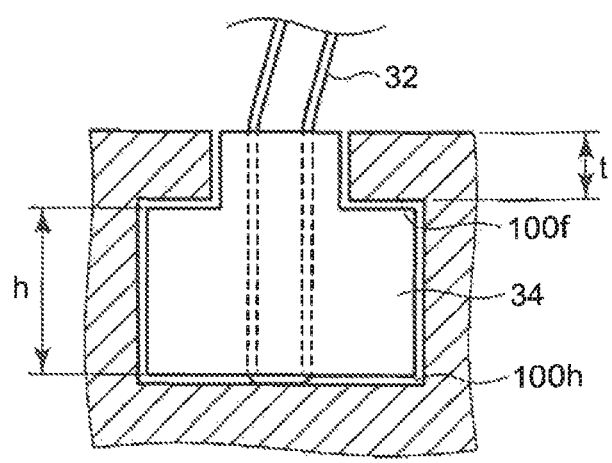
FIG. 13D is a diagram that illustrates the suture anchor fixed to the bottomed hole.

FIG. 11A is a diagram that illustrates a bottomed hole 100h for placing a suture anchor 34 and a probe 14p according to the third embodiment, and FIG. 11B is a diagram that illustrates an external configuration of the probe 14p. FIG. 12A is a diagram that illustrates a state where the probe 14p is pressed against the bone 100, and FIG. 12B is a diagram that illustrates a longitudinal hole formed inside the bone 100 with the probe 14p. FIG. 12C is a diagram that illustrates a state where the probe 14p is rotated inside the longitudinal hole, and FIG. 12D is a diagram that illustrates a state where the bottomed hole 100h is formed with the probe 14p. FIG. 13A is a diagram when the formed bottomed hole 100h is viewed in the direction of a hole entrance, and FIG. 13B is a diagram that illustrates a state where the suture anchor 34 is inserted into the bottomed hole 100h. FIG. 13C is a diagram that illustrates a state where the suture anchor 34 inserted into the bottomed hole 100h is rotated, and FIG. 13D is a diagram that illustrates the suture anchor 34 fixed to the bottomed hole 100h.

The suture anchor 31 can be provided with helical screw threads, and the suture anchor 33 is provided with continuous projections that function as a barb, whereby they are fixed without being removed after it is placed in a bottomed hole.

As illustrated in FIG. 11B, by using the probe 14p that has a rectangular distal end that expands outward from opposite sides a probe base part 14n, the distal end having a cross-sectional area larger than a cross-sectional area of an axis of the probe base part 14n, a bottomed hole 100h in which the cross-sectional area of the inside of the bottomed hole 100h is larger than a hole entrance of a hole 100e (the hole area) is formed. The suture anchor 34 having no helical screw threads or barbs and having an anchor (end button) in the same shape as that of the distal end of the probe 14p is fixed to the bottomed hole 100h. The probe base part 14n is the same as the above-described probe 14 illustrated in FIG. 2 or is integrally connected to the probe 14.

First, as illustrated in FIG. 12A, the distal end of the probe 14p that oscillates with ultrasound waves is pressed against the bone 100. Mechanical cutting is conducted due to a hammering operation of the probe 14p and, as illustrated in FIG. 12B, a longitudinal hole is formed inside the bone 100 through the hole 100e. Here, the probe 14p digs a longitudinal hole until an upper wall 100f of the bottomed hole 100h illustrated in FIG. 13D has a thickness t so as to be tolerant of tension applied to the suture anchor 34. The depth of the bottomed hole 100h is a depth that combines at least the thickness t, a height h of the suture anchor 34, and a space for rotation.

Then, as illustrated in FIG. 12C, while cutting is conducted inside the longitudinal hole, the probe 14p is rotated by 90 degrees with respect to the longitudinal direction of the hole 100e with the probe base part 14n as a center. Then, as illustrated in FIG. 12D, cutting is conducted by reciprocating along the width of the hole in the longitudinal direction of the hole 100e, and the bottomed hole 100h is formed as illustrated in FIG. 13A.

As illustrated in FIG. 13B, the suture anchor 34 is inserted into the bottomed hole 100h through the hole 100e, is rotated by 90 degrees with respect to the longitudinal direction of the hole 100e, and is fixed at the position illustrated in FIG. 13C. The suture anchor 34 is formed in substantially the same shape as that of the distal end part of the probe 14p, is insertable through the hole 100e, and is formed to have a size such that it is rotatable inside the bottomed hole 100h. The suture anchor 34 illustrated in FIG. 13B is formed in a parallelogram with both side surfaces diagonally cut off when viewed from above so that it is rotatable. Furthermore, the width (the length of the hole 100e in the longitudinal direction) of the suture anchor 34 may be narrower, or corners of both side surfaces may be rounded.

The suture anchor 34 may be implemented as an end button having a simple cuboidal shape that does not need any helical screw threads or barbs.

The probe 14p can be reciprocated to form the cuboidal bottomed hole 100h; however, this is not a limitation. For example, it is possible to use the cut shape obtained when the probe 14p is rotated by 90 degrees with respect to the longitudinal direction of the hole 100e and is stopped in FIG. 12C. That is, as illustrated in FIG. 12C, due to this rotation by 90 degrees, two ¼ cylindrical spaces are formed such that they are symmetry with respect to a point. Both side surfaces of the suture anchor 34 are rounded so as to have the curvature corresponding to that of the curved surface (diameter) of the inner wall surface of the bottomed hole 100h. The suture anchor 34 with the rounded side surfaces is inserted through the hole 100e, is rotated by 90 degrees with respect to the longitudinal direction, and is fixed.

Formation of the bottomed hole 100h is finished halfway, and therefore there is a small amount of bone that has been cut. Thus, it is possible to reduce the time until regeneration of the bone is finished after the suture anchor 34 is fixed.

Furthermore, the shape of the probe described in each of the above embodiments and the modification may be the shape combining each shape, for example, the shape partially combining multiple shapes, such as the shape in which the right half thereof is rectangular and the left half thereof is oval. Moreover, in the configuration described, one bottomed hole is formed at the same time with one probe; for example, a probe may have two or more projections at positions away from each other.

It is possible to provide an ultrasound device that forms a bottomed hole having any cross-sectional shape during a back-and-forth movement due to ultrasound oscillations and suture-anchor fixation for fixing a suture anchor having a cross-sectional surface including a circular shape and a polygonal shape into the bottomed hole by screwing or hammering.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical ultrasound device used for fixation using an anchor, the medical ultrasound device comprising:
    an ultrasound generator configured to generate ultrasound oscillation; and
    an elongated probe including a proximal end and a distal end, the ultrasound oscillation being propagated from the ultrasound generator to the proximal end, the ultrasound oscillation being propagated through oscillation toward the distal end in a longitudinal direction of the probe, wherein:
    a cross-sectional surface of the probe at the distal end is perpendicular to the longitudinal direction, and the cross-sectional surface of the probe has a shape identical to a shape of a cross-sectional surface of the anchor;
    the probe is configured to form a bottomed hole in a bone for placing the anchor and the probe has a shape that is configured to prevent rotation of the anchor in the bottomed hole;
    an area of the cross-sectional surface of the probe at the distal end is larger than an area of a cross-sectional surface of the probe at the proximal end;
    the distal end includes a treatment portion that is configured to cut the bone into a predetermined depth to form a first recessed part having a shape identical to a shape of the treatment portion; and
    the treatment portion is configured to be rotated about an axis along a depth direction in the first recessed part to form a second recessed part larger than the first recessed part.

2. The ultrasound device according to claim 1, wherein the shape of the cross-sectional surface of the probe has one or more angles.

3. The ultrasound device according to claim 1, wherein the shape of the cross-sectional surface of the probe has a curve.

4. The ultrasound device according to claim 1, wherein the shape of the cross-sectional surface of the probe is an elongated circle.

5. The ultrasound device according to claim 1, wherein the probe has a cuboidal shape that extends from a center of the proximal end.

6. The ultrasound device according to claim 1, wherein the treatment portion extends outward relative to the proximal end in a first direction that is perpendicular to the longitudinal direction and a second direction that is different from the first direction.

7. The ultrasound device according to claim 1, wherein the shape of the cross-sectional surface of the probe is a polygon.

8. The ultrasound device according to claim 1, wherein the shape of the cross-sectional surface of the probe is a polygon with rounded corners.

9. An ultrasound device system comprising:
- an ultrasound device configured to form a recessed part in a bone with ultrasound oscillation;
- an anchor that is configured to be fixed in the recessed part of the bone; and
- an anchor fixing tool that includes a retaining part configured to retain the anchor and the anchor fixing tool is configured to rotate and fix the anchor in the recessed part formed in the bone, wherein:
the ultrasound device includes:
- an ultrasound generator configured to generate the ultrasound oscillation;
- a probe having a proximal end and a distal end, the ultrasound oscillation being propagated from the ultrasound generator to the proximal end, the ultrasound oscillation being propagated through oscillation toward the distal end in a longitudinal direction of the probe; and
- a treatment portion that is provided at the distal end, the treatment portion being configured to form the recessed part of the bone;
- a cross-sectional surface of the probe at the distal end that is perpendicular to the longitudinal direction, the cross-sectional surface having a shape identical to a shape of a cross-sectional surface of the anchor, the probe being configured to form a bottomed hole in the bone for placing the anchor;
- an area of the cross-sectional surface of the probe at the distal end is larger than an area of a cross-sectional surface of the probe at the proximal end, and
the treatment portion of the ultrasound device extends outward relative to the proximal end and is formed in a first direction perpendicular to the longitudinal direction and in a second direction different from the first direction.

10. An anchor fixation method using an ultrasound device, the method comprising:
- pressing a distal end of an elongated probe against a bone;
- oscillating the probe with ultrasound waves and propagating oscillation of the ultrasound waves toward the distal end of the probe along the longitudinal direction;
- crushing the bone with a surface of the probe in contact with the bone and forming a hole entrance; and
- forming a bottomed hole in the bone by rotating the probe to a predetermined depth in the bone, the bottomed hole having a surface with a shape identical to a shape of a cross-sectional surface of an anchor to place and prevent rotation of the anchor in the bottomed hole; wherein:
the probe has a proximal end on an opposite side of the distal end, an area of a cross-sectional surface of the probe at the distal end is larger than an area of a cross-sectional surface of the probe at the proximal end, and the probe has a cuboidal shape that extends from a center of the proximal end; and
an area of a bottom surface of the bottomed hole is larger than an area of the hole entrance.

11. The method according to claim 10, wherein a shape of the bottom surface of the bottomed hole is identical to a cross-sectional shape of the distal end of the probe.

12. The method according to claim 10, wherein:
the bottom surface of the bottomed hole has a polygonal shape, and
when the anchor is fixed, one surface of the anchor is disposed in a direction that intersects with a direction of tension applied to the anchor.

* * * * *